United States Patent
Kuth et al.

(10) Patent No.: US 8,187,166 B2
(45) Date of Patent: *May 29, 2012

(54) MINIMALLY INVASIVE MEDICAL SYSTEM EMPLOYING A MAGNETICALLY CONTROLLED ENDO-ROBOT

(75) Inventors: Rainer Kuth, Herzogenaurach (DE); Thomas Rupprecht, Uttenreuth (DE); Maren Wagner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 3702 days.

This patent is subject to a terminal disclaimer.

(21) Appl. No.: 10/231,311

(22) Filed: Aug. 29, 2002

(65) Prior Publication Data

US 2003/0060702 A1      Mar. 27, 2003

(30) Foreign Application Priority Data

Aug. 29, 2001   (DE) .................................. 101 42 253

(51) Int. Cl.
   *A61B 1/00*   (2006.01)
(52) U.S. Cl. ......................................... 600/101
(58) Field of Classification Search .................. 600/101, 600/109, 117, 118, 424; 606/130
   See application file for complete search history.

(56) References Cited

U.S. PATENT DOCUMENTS

| | | | | |
|---|---|---|---|---|
| 5,681,260 A | * | 10/1997 | Ueda et al. | 600/114 |
| 5,708,359 A | * | 1/1998 | Gregory et al. | 324/309 |
| 5,805,137 A | * | 9/1998 | Yasutake | 345/156 |
| 6,240,312 B1 | * | 5/2001 | Alfano et al. | 600/476 |
| 6,261,247 B1 | * | 7/2001 | Ishikawa et al. | 600/587 |
| 2005/0192660 A1 | * | 9/2005 | Abraham-Fuchs et al. | 623/1.11 |
| 2005/0209682 A1 | * | 9/2005 | Abraham-Fuchs et al. | 623/1.15 |

FOREIGN PATENT DOCUMENTS

| | | |
|---|---|---|
| DE | 100 28 078 | 3/2001 |
| WO | WO 00/60996 | 10/2000 |

* cited by examiner

*Primary Examiner* — Tse Chen
*Assistant Examiner* — Elmer Chao
(74) *Attorney, Agent, or Firm* — Schiff Hardin LLP

(57) ABSTRACT

A system for the implementation of minimally invasive diagnoses and interventions in the inside of the body of a patient has an endo-robot that has a linear magnet and carries measurement instruments and/or instruments for taking specimens and/or for treatment. The endo-robot is freely mobile within the body of a patient. A magnet system accepts the examination region of the patient and generates a 3D gradient field for remotely-controls movement and orientation of the endo-robot in the patient's body by interaction with the linear magnet.

22 Claims, 1 Drawing Sheet

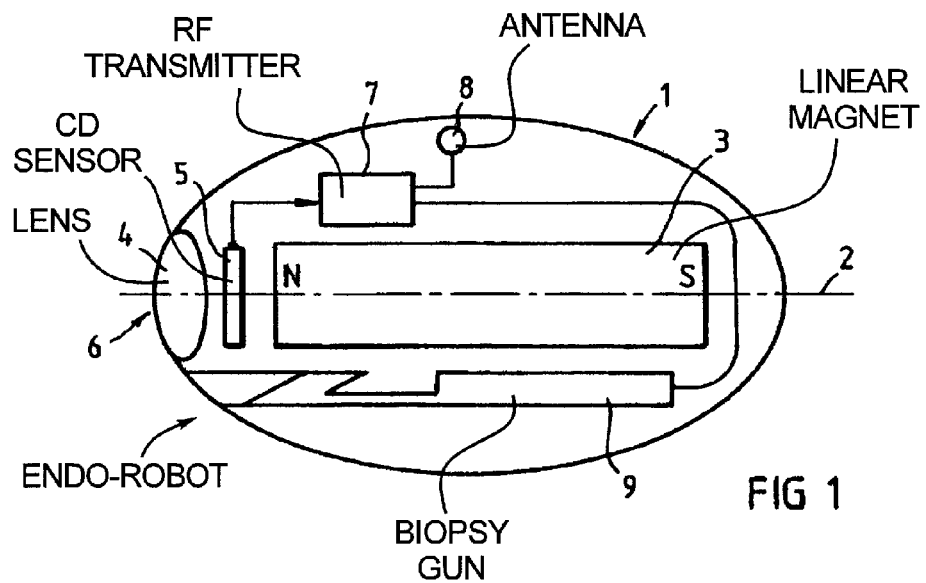
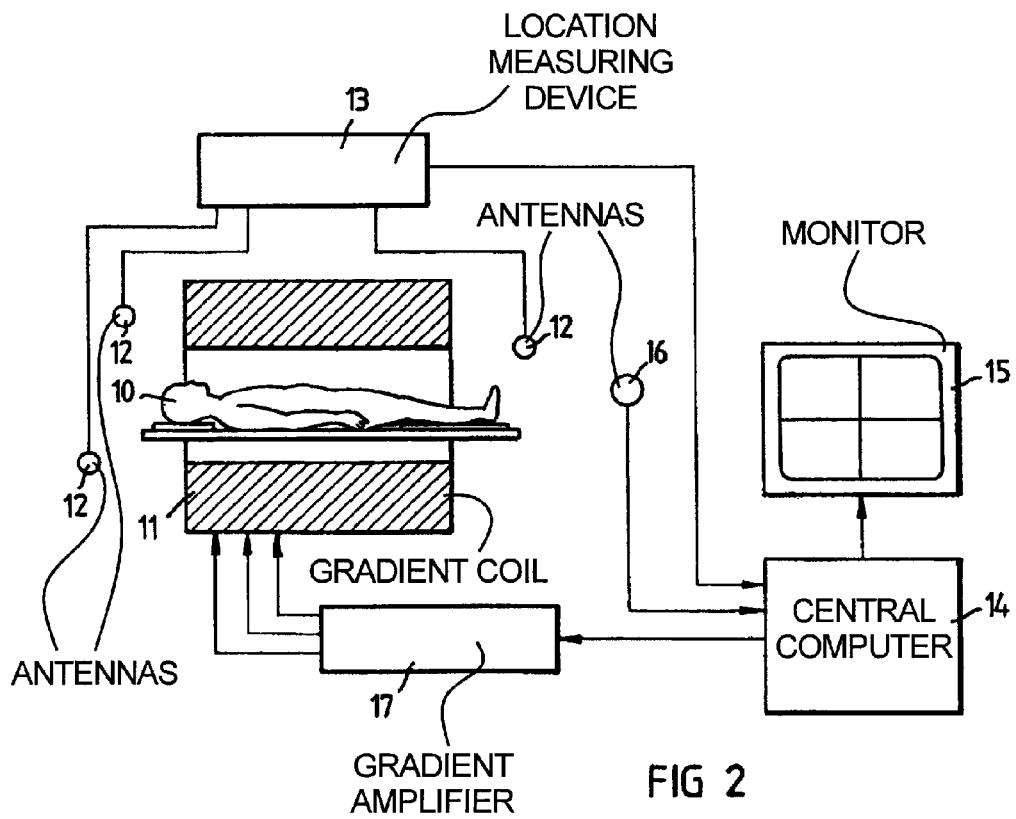

MINIMALLY INVASIVE MEDICAL SYSTEM EMPLOYING A MAGNETICALLY CONTROLLED ENDO-ROBOT

BACKGROUND OF THE INVENTION

1. Field of the Invention

The present invention is directed to a device for the implementation of minimally invasive diagnoses and interventions in the inside of the body of a patient, having a carrier head that preferably carries measurement instruments and/or instruments for obtaining a specimen and/or for treatment.

2. Description of the Prior Art

Conventionally, such minimally invasive diagnoses and interventions in the inside of the body are implemented with the assistance of rigid or flexible endoscopes, laparoscopes or catheters. These techniques are characterized by the forces required for the navigation of the carrier head in the body being exerted from the outside by the surgeon's hand. This technique encounters implementation limits for, among other things, applications in the small intestine, which is 7 to 11 meters long in adults.

A method disclosed in PCT Application WO 00/60996 yields only a slight improvement in this context, whereby the tip of the catheter is steered into the desired direction at intersections of the vessels or openings by an external magnetic field. In this case, as well, there is the problem of the long extent of the device and the problem of manual application of force for the navigation. When many curves and branchings must be traversed in this case, and such high friction ultimately occurs so that a displacement over greater distances is no longer possible at all.

German OS 100 28 078 discloses an endoscope that can be completely swallowed and that comprises two bendable parts and one flexible part. Drive wires lying in the parts are heated via electromagnetic signals by means of an external control device, causing the drive wires to subsequently bend. The parts thus can follow a curvature of the body cavity.

SUMMARY OF THE INVENTION

An object of the present invention is to provide a device of the type initially described wherein the carrier head is freely navigable in the inside of the body without a fixed connection to the outside.

This object is achieved in accordance with the invention in a device of the type initially generally described wherein a magnet system is provided that accepts the examination region of the patient and generates a 3D gradient field for remote-controlled movement and orientation of the carrier head in the body, the carrier head being provided with a linear magnet and being fashioned as a freely mobile endo-robot.

Such field generators for generating a 3D gradient field are known from MR technology. The endo-robot contains a bar magnet or a drivable, approximately linear coil, so that a linear force and a torque can be generated by interaction with the gradient field as long as the bar magnet and gradient field are not co-linear. In addition to defining the torque, the steepness of the gradient also defines the translational force in the magnet or coil axis.

It has proven especially expedient for the magnet system also to generate a static basic field for compensating the force of gravity on the endo-robot, preferably by means of a superconducting basic field magnet, particularly a basic field magnet composed of a high-temperature superconductor. This compensation of the force of gravity exerted on the endo-robot makes it possible to move this in a free-floating manner in a body channel (intestine, blood vessel or the like), so that it can neither become entangled nor can the projecting instruments or tools (if present) lead to injury in the body.

It has also proven especially expedient to control the static basic field for compensating changes in weight of the endo-robot when loading and unloading. Such loading and unloading can, for example, ensue when taking specimens with, for example, a biopsy device installed in the endo-robot or when administering medications, whereby such medications can be designationally released at specific locations, for example tumors, with the assistance of the inventive endo-robot.

Since the homogeneity volume in the static field of the magnet system usually is very small, for such compensation in a further embodiment of the invention the patient and the magnet system are movable relative to one another, in particular the patient is arranged on a patient bed that is adjustable in the magnet system. Given ongoing movement of the endo-robot in the body, by means of repositioning of the patient the respective position of the endo-robot can be optimally maintained in the middle of the homogeneity volume.

Advantageously, the endo-robot is navigated with a force input device, for example a device referred to as a 6D mouse. The gradient direction—that corresponds to the superimposition of the three individual systems—can thereby be determined by tilting toward the front/back and right/left as well as by pressing or lifting, and the amplitude can be determined by turning the input lever. It is advantageous when the forces exerted on the input device correspond to or are proportional to the force exerted onto the instrument.

In a further embodiment of the invention, the endo-robot has an illumination device for lighting its surroundings. This illumination device can be extremely bright given employment of infrared LEDs but—in this case—enables only a black-and-white reception with a video camera, which is likewise preferably built into the endo-robot. In order to also obtain color images, high-performance LEDs in three colors or micro-fluorescent lamps can be employed. Such components, however, have the disadvantage of requiring high ignition voltages.

The images of the aforementioned video camera preferably are transmitted by radio from inside of the body to a monitor, with the video camera being equipped with a device that enables rotation of the image around the central axis.

In another embodiment of the invention, the endo-robot can be provided with a localization device that, in particular, operates via transponders in order to enable a positional presentation on a picture screen displaying the anatomical environment. For example, the anatomical environment can be presented in tomograms as in known commercial navigation systems.

The endo-robot can be operated in a helicopter mode wherein the gradient field is regulated, with the position of the endo-robot being acquired by transponders, so that the endo-robot stands still or can be linearly moved a predetermined distance.

The endo-robot can have an installed accumulator that can be recharged via an external alternating field for the power supply of the endo-robot.

The inventive endo-robot also can be utilized without any additional measurement instruments, instruments for taking specimens and treatment instruments, for example for opening blocked channels, for example blood vessels. It is made more advantageous and versatile, however, by installing tool arms with knives, forceps, loops (snares) or the like as well as measurement probes having sensors for temperature, electrical conductivity, pH value, pressure, as well as chemical sensors.

In addition to the aforementioned installation of a biopsy device as well as devices for targeted administration of medications, the endo-robot can be advantageously provided with an intervention laser.

The inventive endo-robot can be introduced into the inside of the body (brain, abdominal cavity, lung or the like) via a sluice, as is known from laparoscopy.

DESCRIPTION OF THE DRAWINGS

FIG. 1 is a schematic illustration of the structure of an inventive endo-robot.

FIG. 2 is a schematic illustration of the overall inventive system with the magnet system and the control devices for the control of the endo-robot in the body of a patient.

DESCRIPTION OF THE PREFERRED EMBODIMENTS

The endo-robot 1 shown in FIG. 1 has an ellipsoidal housing in which a bar magnet 3 is arranged co-linear with the major axis 2. A video camera 6 composed of a lens 4 and a CD sensor 5 registers images that are transmitted toward the outside with a radio-frequency transmitter 7 and an antenna 8. Drive of various measurement instruments, instruments for taking specimens, or treatment instruments also ensues by radio, i.e. vie the same antenna 8. Only a biopsy gun 9 as an example is shown in the exemplary embodiment of FIG. 1, but the endo-robot 1 can be equipped with a wide variety of surgical implements, tools and sensors.

Referring to FIG. 2, the positional control of an inventive endo-robot in a system is shown. The patient 10 lies in a gradient coil 11, which is shown only in section, and is known from commercial MR scanners. The region of the body to be examined, i.e. the region in which the endo-robot 1 according to FIG. 1 should move, is located in the linearity volume of the gradient coil 11. Antennas 12 pick up signals of the transponder or transponders of the endo-robot 1 and forward them to the location measuring device 13. This forwards the 3D location to the central computer 14 either cyclically or given changes compared to previous values. The computer 14 presents tomograms of a 3D dataset on the monitor 15 in respective axial, coronary and sagittal planes. Images from the video camera are received via radio with a further antenna 16 and are likewise displayed on the monitor 15. A 3-channel gradient amplifier 17 drives the gradient coils via the central computer 14. The type of input device, preferably fashioned as 6D mouse, and the basic field magnet for compensating the effect of gravity on the endo-robot, are not shown.

The endo-robot 1 preferably is fashioned such that it can be sterilized. Different sterilization methods can be utilized dependent on the structure and on the dependability of the seal of the inside of the endo-robot. The optimum autoclaving at 132° C. and a few bars pressure usually is not sufficient given the presence of a number of interior cavities, and particularly when there are also seals toward the outside. A pressure-free cleaning as well as a plasma sterilization or cold gas sterilization could be used given a water-tight housing.

By providing a magnet secured outside at the body, for example at a belt, the endo-robot 1 can be "parked" in the body, so that the patient—after the static field magnet has been ramped down with a flux pump—can exit the magnet system in order to undergo a further examination using the endo-robot (still located in the body) after a prescribed time duration, for example even on the next day.

Although modifications and changes may be suggested by those skilled in the art, it is the intention of the inventors to embody within the patent warranted hereon all changes and modifications as reasonably and properly come within the scope of their contribution to the art.

We claim:

1. A system for conducting a minimally invasive medical procedure in an interior of a body of a patient, comprising:
   an endo-robot having a linear magnet and being adapted for free mobility in an interior of a body of a patient; and
   a housing comprising a magnet system, said housing and said magnet system forming a receptacle configured to receive at least an examination region of said patient therein, said magnet system generating a three-dimensional gradient magnetic field for remotely controlling movement and orientation of said endo-robot in said body, by interaction with said linear magnet.

2. A system as claimed in claim 1 wherein said endo-robot contains a bar magnet as said linear magnet.

3. A system as claimed in claim 1 wherein said endo-robot contains a controllable substantially linear coil as said linear magnet.

4. A system as claimed in claim 1 wherein said magnet system comprises a magnet for generating a static, basic magnetic field for compensating for the force of gravity acting on said endo-robot.

5. A system as claimed in claim 4 wherein said magnet for generating said static basic magnetic field is a superconducting magnet.

6. A system as claimed in claim 5 wherein said superconducting magnet is a magnet composed of a high-temperature superconductor.

7. A system as claimed in claim 4 comprising a control unit for controlling said magnet for generating said static basic magnetic field to compensate for a weight change experienced by said endo-robot during said medical procedure.

8. A system as claimed in claim 1 further comprising an arrangement for interacting with said patient for moving said patient relative to said magnet system.

9. A system as claimed in claim 8 wherein said arrangement comprises a patient bed, adapted to receive said patient thereon, displaceable in said magnet system.

10. A system as claimed in claim 1 wherein said endo-robot comprises an illumination device adapted to illuminate an environment surrounding said endo-robot in said body.

11. A system as claimed in claim 1 wherein said endo-robot comprises a video camera, and a transmission system for transmitting video signals from said video camera out of said patient.

12. A system as claimed in claim 1 further comprising a display on which an anatomical environment of said endo-robot in said patient is displayed, and wherein said endo-robot comprises a localization device allowing a presentation of position of said endo-robot on said display in said anatomical environment.

13. A system as claimed in claim 12 wherein said localization device comprises at least one transponder.

14. A system as claimed in claim 1 wherein said endo-robot contains an accumulator for supplying power within said endo-robot, said accumulator being rechargeable by interaction with an externally-applied alternating field.

15. A system as claimed in claim 1 further comprises a control unit for controlling said gradient magnetic field to operate said endo-robot in a helicopter mode, allowing at least one of causing said endo-robot to stand still in said patient and to move a prescribed distance in said patient.

16. A system as claimed in claim 1 further comprising an input device for adjusting said gradient magnetic field to control movement and orientation of said endo-robot in said patient by causing a force to be exerted on said endo-robot that corresponds to a force exerted on said input device.

17. A system as claimed in claim 16 wherein said input device is a 6D mouse.

18. A system as claimed in claim 1 wherein said endo-robot comprises an intervention laser.

19. A system as claimed in claim 1 wherein said endo-robot includes a release device for releasing a substance selected from the group consisting of solid medications, liquid medications, gaseous medications, contrast agents and irradiation therapy marking aids, at a specific location within said body.

20. A system as claimed in claim 1 wherein said endo-robot is sterilizeable.

21. A system as claimed in claim 1 further comprising a magnet adapted to be secured at an exterior of the body of said patient for causing said endo-robot to be maintained in a parking position in said patient after said patient exits said magnet system.

22. A system as claimed in claim 1 comprising at least one medical device carried by said endo-robot, selected from the group consisting of measurement devices, instruments, specimen devices and treatment devices.

* * * * *